United States Patent [19]
Drillien et al.

[11] Patent Number: 5,830,688
[45] Date of Patent: Nov. 3, 1998

[54] DNA SEQUENCES, VECTORS, RECOMBINANT VIRUSES AND METHOD WHICH EMPLOYS RECOMBINANT VACCINIA VIRUSES CAPABLE OF MULIPLYING IN CHO CELLS

[75] Inventors: Robert Drillien, Strasbourg; Daniéle Spehner, Eckbolsheim, both of France

[73] Assignee: Transgene, S.A., Paris, France

[21] Appl. No.: 478,092

[22] Filed: Jun. 7, 1995

Related U.S. Application Data

[63] Continuation of Ser. No. 43,772, Apr. 6, 1993, abandoned, which is a continuation of Ser. No. 697,483, May 2, 1991, abandoned, which is a continuation of Ser. No. 100,331, Sep. 23, 1987, abandoned.

[30] Foreign Application Priority Data

Sep. 23, 1986 [FR] France .................................. 8613272

[51] Int. Cl.$^6$ .............................. C12P 21/06; C12N 7/00; C12N 15/00; C07H 21/04
[52] U.S. Cl. .................. 435/69.1; 435/235.1; 435/172.3; 435/320.1; 435/240.2; 435/70.1; 435/70.3; 435/70.21; 530/350; 536/23.77; 536/23.1; 536/27
[58] Field of Search ................................ 435/235.1, 69.1, 435/172.3, 320.1, 240.2, 32, 34, 9, 27, 57, 61, 70.1; 530/350; 536/23.72, 23.1, 27

[56] References Cited

U.S. PATENT DOCUMENTS 4,769,330  9/1988  Paoletti et al. ........................ 435/172.3

OTHER PUBLICATIONS

Mackett, M. et al., 1982, P.N.A.S., vol. 79, pp. 7415–7419.
Kotwal, G. et al., 1988, Vivogy, vol. 167, pp. 524–537.
Miner, J. et al, 1990, Virus Genes, pp. 355–359.
Pickup, D. et al., 1984 P.N.A.S, vol. 81, pp. 6817–6821.
Mackett, M. et al, 1979, J. Gen. Virol., vol. 45, pp. 683–701
Drillien, R. et al, 1983, Virology, vol. 131, pp. 385–393.
Dijkema et al, 1985, EMB, vol. 4(3), Pp.761–767. (Abstract).
Susada et al, 1987, Cell Structure Function, vol. 12(2), pp. 205–217. (Abstract).

*Primary Examiner*—Marian C. Knode
*Assistant Examiner*—Ali R. Salimi
*Attorney, Agent, or Firm*—Burns, Doane, Swecker & Mathis, L.L.P.

[57] ABSTRACT

The DNA sequence of this invention, isolated from cowpox virus, participates in the multiplication of this virus in CHO cells. This DNA may be incorporated into vectors and recombinant viruses (e.g., recombinant vaccinia viruses). Such recombinant viruses are capable of multiplying in CHO cells.

14 Claims, 8 Drawing Sheets

```
                                                  30                              60           90
GTG TTA ACG GAG GTG TAA ACT CTG GAG TTA ATA AAA CAC TAA ATT TTT TAT TAA TAA TTG TAC AAG TTT TTG ATC TGG TAT
                                                                                                          180
AAA TAC ATT CAA AAA TGA TAA TTT AAT GAC ATT AGT TGT GCG GGT GTA TAG AGT TCA CAG TAG CTC ATT CAC TTC TAT TCA GTC AAA ATG
                                                                                                                    Met
         210                     240                     270
TTT GAT TAT CTG GAA AAT GAG GAG GTG GCT CTC GAT GAA CTT AAA CAG ATG TTG AGA AGA GAT CCT AAT GAT ACC AGG AAC CAA TTC
Phe Asp Tyr Leu Glu Asn Glu Glu Val Ala Leu Asp Glu Leu Lys Gln Met Leu Arg Arg Asp Pro Asn Asp Thr Arg Asn Gln Phe
         300                     330                     360
AAG AAT GCT CTA CAT GCA TAC CTT TTC AAT GAG CAC GTC AAA CTA CTA GTT ACT GGT AGT GAC ATG CCA
Lys Asn Ala Leu His Ala Tyr Leu Phe Asn Glu His Val Lys Leu Leu Val Thr Gly Ser Asp Met Pro
         390                     420                     450
TTA CAC AAA AAT TGG AGA CAG CTT ACT CCA TTA GGG GAA TAC ACA AGA CAT AAT GTT AAA GAT ATT ATA GTT CTA
Leu His Lys Asn Trp Arg Gln Leu Thr Pro Leu Gly Glu Tyr Thr Arg His Asn Val Lys Asp Ile Ile Val Leu
         480                     510                     540
CTA GAA GCT ACT GGA TAT AAT AAC ATA GAC TTT AAT ATA TTC ACC TAT ATG AAA TCC TTG ATA GAC TTG ATA AAG GTA
Leu Glu Ala Thr Gly Tyr Asn Asn Ile Asp Phe Asn Ile Phe Thr Tyr Met Lys Ser Leu Ile Asp Leu Ile Lys Val
         570                     600                     630
TTG GTA GAA CAT GGA TTT GAT TTT AGT GTT AAA TGC GAA GTT ATA CAT CAT ATA GAA GAG GAT ATT GTA ACA GTA ATG GAT CCT GTT
Leu Val Glu His Gly Phe Asp Phe Ser Val Lys Cys Glu Val Ile His His Ile Glu Glu Asp Ile Val Thr Val Met Asp Pro Val
         660                     690                     720
GAA ATT GAT TTA TTC ATA GAA AAT GGA TGC AGT GTT ATT TAT GAG GAC GAG GAT TAC GGA TAC GCG TAT GAA GAA TAT CAC
Glu Ile Asp Leu Phe Ile Glu Asn Gly Cys Ser Val Ile Tyr Glu Asp Glu Asp Tyr Gly Tyr Ala Tyr Glu Glu Tyr His
         750                     780                     810
TCA CAA AAT GAC GAT TAT CAA CCA CGA AAT TGC GGT ACA GTA TTA CAT ATC TCT CAT CTG TAT TCA GAG TCG GAT TCG AGA
Ser Gln Asn Asp Asp Tyr Gln Pro Arg Asn Cys Gly Thr Val Leu His Ile Ile Ser His Leu Tyr Ser Glu Ser Asp Ser Arg
```

FIG. 6A

```
TCA TGT GTG AAC CCG GAA GTT GTT AAA TGT CTG ATT AAT CAT GGA ATC AAC CCA TCT ATA GAT AAA AAC TAT TGT ACA GCT CTT
Ser Cys Val Asn Pro Glu Val Val Lys Cys Leu Ile Asn His Gly Ile Asn Pro Ser Ile Asp Lys Asn Tyr Cys Thr Ala Leu
                                                    840                     870                                900
                                                                                                                CAA
                                                                                                                Gln

TAT TAT ATT AAG TCA TCT CAT ATA GAT ATA GAC ATC GTT AAA TTG TTA ATG AAA GGA ATA GAT AAC ACG GCT TAT TCA TAT ATA GAC GAT
Tyr Tyr Ile Lys Ser Ser His Ile Asp Ile Asp Ile Val Lys Leu Leu Met Lys Gly Ile Asp Asn Thr Ala Tyr Ser Tyr Ile Asp Asp
                    930                             960                                                        990

CTA ACA TGT TGT ACT CGA ATT ATG GCT GAT TAT CTA AAT AGT GAT TAT AGA AAA GAT GTA GAT TTA GAT TTG GTC AAA TTG
Leu Thr Cys Cys Thr Arg Ile Met Ala Asp Tyr Leu Asn Ser Asp Tyr Arg Lys Asp Val Asp Leu Asp Leu Val Lys Leu
                    1020                            1050                                                1080

TTT TTG GAG AAT GGA AAA CCG CAC CAC ATG TGT AGT ATT GTA CCA CTA CTA TGG AGA AAT GAT AAG GAA ACC ATC TCT TTG ATA ATT
Phe Leu Glu Asn Gly Lys Pro His His Met Cys Ser Ile Val Pro Leu Leu Trp Arg Asn Asp Lys Glu Thr Ile Ser Leu Ile Leu
                    1110                            1140                                                1170
                                                                                                                    AAA
                                                                                                                    Lys

ACA ATG AAC TCG GAT GTC CTC CAA CAT ATA CTA ATT GAG TAT ATA ACA TTC AGC GAT ATC GAT ATC TCT CTA GTG GAA TAC ATG TTG GAA
Thr Met Asn Ser Asp Val Leu Gln His Ile Leu Ile Glu Tyr Ile Thr Phe Ser Asp Ile Asp Ile Ser Leu Val Glu Tyr Met Leu Glu
                    1200                            1230                                                1260

TAT GGA GCT GTG GTA AAT GAG GCT ATT CAC GGA TAC GGT GAT ATT AAT ATT TTT AAA AAT ATT GAT TCT TAC ACG ATG AAA TAT CTA AAA AAG
Tyr Gly Ala Val Val Asn Glu Ala Ile His Gly Tyr Gly Asp Ile Asn Ile Phe Lys Asn Ile Asp Ser Tyr Thr Met Lys Tyr Leu Lys Lys
                    1290                            1320                                                1350

GAA GGG GGA GAT GCC GTC AAT CAT CTC GAT GAT GGA GAG ATC CCG ATT GGA CAC CTA TGT CTA TGT AAA TCC AAC TAT GGA CGT TAT TTC TAC
Glu Gly Gly Asp Ala Val Asn His Leu Asp Asp Gly Glu Ile Pro Ile Gly His Leu Cys Leu Cys Lys Ser Asn Tyr Gly Arg Tyr Phe Tyr
                    1380                            1410                                                1440

ACT GAT ACA TAC AGA CAG GGT TTT CGT GAT ATG TCT GAT TAT GCT CCA ATT CTT AGT ACT ATA AAC ATT TGC CTA CCT TAT CTT AAA GAC
Thr Asp Thr Tyr Arg Gln Gly Phe Arg Asp Met Ser Asp Tyr Ala Pro Ile Leu Ser Thr Ile Asn Ile Cys Leu Pro Tyr Leu Lys Asp
                    1470                            1500                                                1530

ATT AAC ATG ATT GAC AAA CGA GGA GAA ACA CTT CTT CAC CAA GCT GTT AGA TAT AAT AAA CAA TCT AGT CTA GTG TCT TTA CTG CTA GAA TCC
Ile Asn Met Ile Asp Lys Arg Gly Glu Thr Leu Leu His Gln Ala Val Arg Tyr Asn Lys Gln Ser Ser Leu Val Ser Leu Leu Leu Glu Ser
                    1560                            1590                                                1620

FIG. 6B
```

```
GGT TCA GAT GTC AAC ATT AGA TCA AAT AAC GGA TAT ACA TGT ATA GCC ATT GCA GAA TCT AGA AAC ATT GAA CTG AAC ATG
Gly Ser Asp Val Asn Ile Arg Ser Asn Asn Gly Tyr Thr Cys Ile Ala Ile Ala Glu Ser Arg Asn Ile Glu Leu Asn Met
                                     1650                            1680                               1710

CTA TTA TGT CAT AAA CCT ACA TTA GAT TGT GTG ATT GAT TCA TTG AGA GAA ATA TCT AAC ATA GTA GAT AAT GCC TAT GCT ATA AAA CAA
Leu Leu Cys His Lys Pro Thr Leu Asp Cys Val Ile Asp Ser Leu Arg Glu Ile Ser Asn Ile Val Asp Asn Ala Tyr Ala Ile Lys Gln
                1740                                      1770                               1800

TGT ATT GCC TAT GAC ATA ATT ATA TCG TCT TGT ATA AAG ATT CCA GAG TCC ATA AGT AAA CAC TAT AAT GAT TAT ATA GAT ATT
Cys Ile Ala Tyr Asp Ile Ile Ile Ser Ser Cys Ile Lys Ile Pro Glu Ser Ile Ser Lys His Tyr Asn Asp Tyr Ile Asp Ile
                  1830                            1860                            1890

TGC AAT CAA GAA TTG AAC GAG ATG ATA ATA GTG GGA GGC GGG ACT ATG TTC TCA TTA ATA TTT ACT GAT CAT GGA GCT AAA ATT
Cys Asn Gln Glu Leu Asn Glu Met Ile Ile Val Gly Gly Gly Thr Met Phe Ser Leu Ile Phe Thr Asp His Gly Ala Lys Ile
                         1920                            1950                            1980

ATT CAT CGG TAT GCC AAT AAT CCA GAA TTA CGT GCG TAT TAT GAG TCA AAA CAA TCA GTT GAT GAC AAT ACC TAT ATT TCC
Ile His Arg Tyr Ala Asn Asn Pro Glu Leu Arg Ala Tyr Tyr Glu Ser Lys Gln Ser Val Asp Asp Asn Thr Tyr Ile Ser
           2010                            2040                            2070

AAT GCG ATA GTG AAG CAT AAT AAA ATT CAT AAA AAC ATA GAA TCA GTT GAT GAC AAT ACC TAC ATT TCT AAT TTG CCT TAT ACC ATC AAA
Asn Ala Ile Val Lys His Asn Lys Ile His Lys Asn Ile Glu Ser Val Asp Asp Asn Thr Tyr Ile Ser Asn Leu Pro Tyr Thr Ile Lys
                         2100                            2130                            2160

TAC AAA ATA TTC GAG CAA CAA TAA GTA TTT TTT ATA CCT TTA AAA TTG ATA AAT AAA TTT CTA GTG ATA TTT TGG CAA GAT GAG AAT
Tyr Lys Ile Phe Glu Gln Gln End                                                                                    2250
                2190                           2220

CCT ATT TCT CAT CGC TTT CAG TGG GTG TGT TCA CTC ATA TGT TAA C
                                     2280
```

FIG. 6C

DNA SEQUENCES, VECTORS, RECOMBINANT VIRUSES AND METHOD WHICH EMPLOYS RECOMBINANT VACCINIA VIRUSES CAPABLE OF MULIPLYING IN CHO CELLS

This application is a continuation of application Ser. No. 08/043,772, filed Apr. 6, 1993, now abandoned, which is a continuation of application Ser. No. 07/697,483 filed May 2, 1991 now abandoned, which is a continuation of application Ser. No. 07/100,331 filed Sep. 23, 1987 now abandoned.

Vaccinia virus has increasingly been used as expression vector in animal cells since methods specific to this system were developed (Panicali and Paoletti, 1982; Macket et al., 1982, Smith et al., 1983; Panicali et al.; Kieny et al., 1984). The construction of recombinant viruses of vaccinia virus containing genes which code for proteins of medical or veterinary interest is particularly sought. The synthesis of the foreign protein whose gene has been integrated into the genome of vaccinia virus can then be obtained in in vitro cell culture or after inoculating into a living organism, depending on the object pursued. One of the advantages of vaccinia virus as the vector is its capacity to multiply in a large number of different types of cells.

However, there are some exceptions to this rule; in particular, the wild type of vaccinia virus is incapable of multiplying in a Chinese hamster ovary, CHO, cell line (Drillien, Spehner and Kirn, 1978). Thus, CHO cells constitute one of the most promising systems for the synthesis of proteins in mammalian cells. In fact, these cells can be cultured easily; they have a short generation time and their genetics are the best known of all similar systems.

The present invention relates to the modification of the vaccinia virus by integrating into its genome a foreign gene which gives it the capacity to multiply in CHO cells. The gene which provides this new host specificity is derived from the cowpox virus (or bovine smallpox, cow virus related to the vaccinia virus) which is capable of multiplying in CHO cells. The genomes of cowpox and of vaccinia virus are very similar particularly in the 100,000 base pairs of the central portion of DNA (Mackett and Archard, 1979). However, the genome of cowpox is larger than that of vaccinia (approximately 230,000 bp instead of 190,000) and the additional genetic information it contains, appears to reside essentially at its ends. The similarity between the genome of vaccinia virus and that of cowpox enables the use of cowpox as the vector naturally adapted to CHO cells to be envisaged.

However, cowpox multiplies at a titer ten times lower than that of vaccinia, which is likely to result in a lower yield of expression of a protein produced by a cowpox recombinant in comparison with a vaccinia recombinant.

Moreover, from the point of view of using viral recombinants for vaccination, it must be emphasized that the use of vaccinia virus is well known and has now enabled smallpox to be eradicated completely.

The present invention relates to the development of a vector which has the known advantages of the vaccinia virus and the capacity of cowpox virus to multiply on CHO cells.

Firstly, the present invention relates to the identification and the localization of the genetic information which gives the cowpox virus the capacity to multiply in CHO cells.

In fact, the studies carried out have made it possible to identify a sequence involved in the multiplication of cowpox virus in CHO cells and which, when transferred into the vaccinia virus, ensures the multiplication of this virus in the CHO cells.

Thus, the invention relates to a DNA sequence isolated especially from cowpox virus and which participates in the multiplication of this virus in CHO cells and which comprises the whole or a functional portion of the sequence shown in FIG. 6 or a functionally equivalent sequence.

It is possible that a portion of this gene, referred to as the "functional portion", is sufficient to provide for the multiplication. It is also possible that mutations or point variations do not modify the function; reference is then made to "functionally equivalent sequence".

Although it is preferred that this DNA sequence contains its own control signals which provide for its expression in CHO cells, this is not indispensable, and placing it under the control of elements having a different origin may be envisaged.

As described above, this DNA sequence is more particularly intended for integration into the vaccinia virus in order to provide for its multiplication in CHO cells. This integration is accomplished by homologous recombination; it is therefore useful to ensure that the DNA sequence in question will contain at least one region homologous to a sequence of the vaccinia virus which could participate in this process of homologous recombination during the intracellular multiplication of the viruses.

In fact, it appears that in the cowpox virus the gene which enables multiplication to occur in CHO cells is surrounded by sequences homologous to the sequences of the vaccinia genome, which enables the preparation of a plasmid recombination vector to be simplified.

As already known in the case of the vaccinia virus, it is possible to insert into the DNA sequence which forms the subject of the invention a gene coding for a protein of industrial value, which is dependent on the control elements providing for its expression in the host cells. This technology has already been described, especially in the following patents: 84/06,499, 84/07,959 and 85/109,225 and can be employed possibly with some adaptations and advantages. In particular, in the preceding constructions, the selection of the recombinant viruses was carried out by inserting the gene to be expressed into the TK gene of vaccinia, which results in the recombinant virus being rendered $TK^-$ and in enabling the selection to be carried out by the known method.

In the present case, it is not indispensable to carry out an insertion into the TK gene because, insofar as the gene coding for the protein of industrial value is linked to the gene providing for the multiplication in CHO cells, only the recombinant viruses can multiply on CHO cells, which allows a "natural" selection of the recombinant viruses to be carried out.

In the latter case, it is preferable that the DNA block containing the genes to be recombined is flanked by sequences homologous to the sequences of vaccinia virus in order that they remain linked during the recombination.

The present invention also relates to CHO cells infected with a recombinant vaccinia virus incorporating a DNA sequence as described above and, in particular, a gene coding for a protein of industrial value and to the corresponding viruses.

The invention also relates to plasmid vectors incorporating a DNA sequence as described above, it being possible for these vectors to be employed in order to carry out the recombination in vivo.

The invention also relates to CHO cells which have been integrated into a DNA sequence according to the present invention and which are capable of ensuring the multiplication of the vaccinia virus in these cells.

Finally, the invention relates to the preparation of proteins of industrial value by culturing CHO cells which are infected by a recombinant virus according to the invention.

The examples below are intended for illustrating the other characteristics and advantages of the present invention.

EXAMPLE 1

Identification of the region of the cowpox virus genome which permits multiplication in CHO cells.

Recombinants between the vaccinia virus and cowpox were selected after mixed infection of chick embryo cells with each of the viruses. Analysis of the DNA of the recombinants shows that the capacity to multiply in CHO cells is associated with the retention of the restriction sites at the left end of the cowpox genome.

Primary chick embryo cells, prepared from 11 to 12-day old embryonated eggs, are simultaneously infected with a temperature-sensitive mutant of the vaccinia virus, tsN7 (Drillien et al., 1982) and cowpox (Brighton strain) at a rate of 2 plaque-forming units (pfu) per cell. Concurrently, other cell lawns are infected with each of these viruses. After one hour of adsorption, the excess unadsorbed virus is removed and fresh medium is added to the cells.

The latter are incubated at 33° C. for one to two days until the entire cell layer undergoes necrosis. The infected cells are then frozen and thawed, and the virus resulting from the infection is titrated at 39.5° C. on thick embryo cells, under a layer of medium containing 1% refined agar. After two days at 39.5° C., a larger number of plaques of the virus is formed on the cell lawns infected with the mixture of the two viruses than on the control lawns (neither the temperature-sensitive mutant of vaccinia virus nor the cowpox gives a significant number of plaques); the plaques which appear from the mixed infection may therefore correspond to recombinants between the cowpox and the vaccinia virus.

Plaques of potential recombinants are then taken again individually, and the virus they contain is amplified by multiplication on chick embryo cells. Their DNA is then purified, cut with restriction enzymes and then analyzed on agarose gel.

Figure 1:
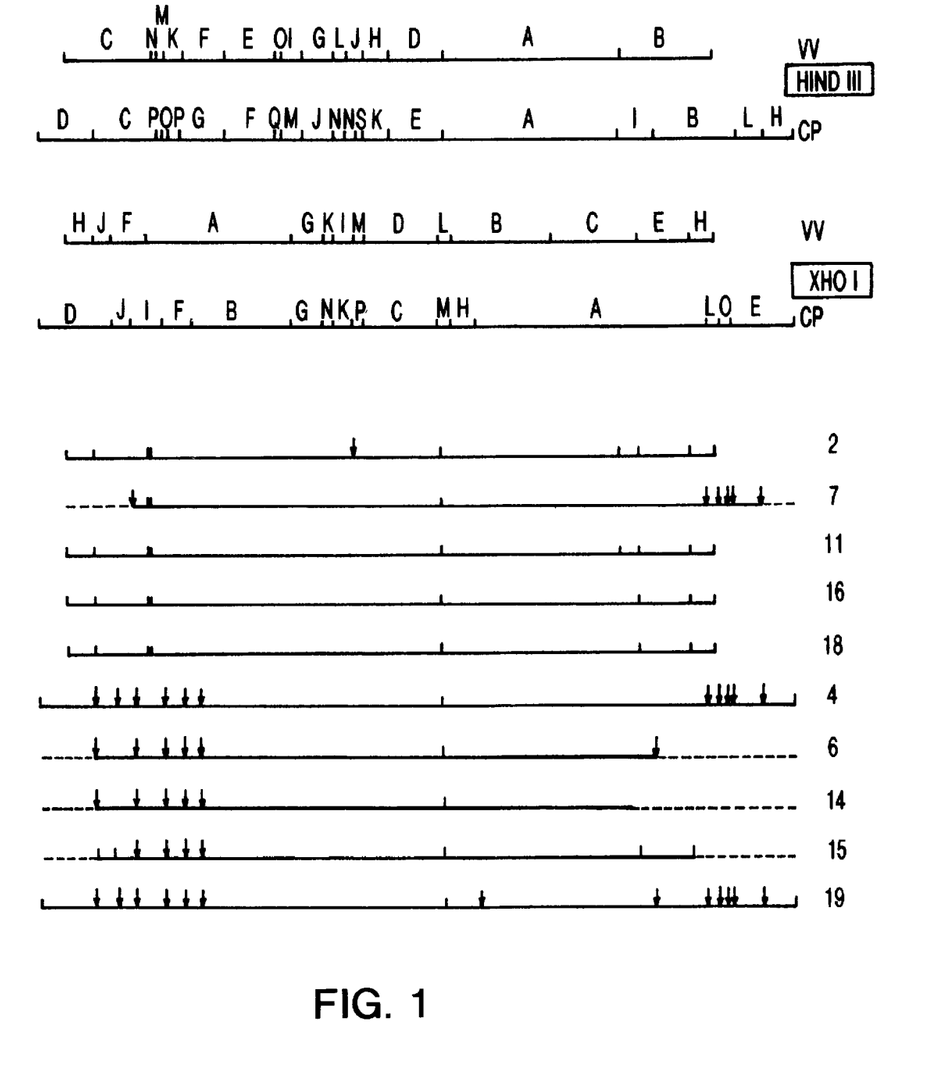
FIG. 1 Restriction maps for the DNA of the recombinants between vaccinia virus and cowpox.

It can be concluded from the restriction profiles that each plaque indeed corresponds to a recombinant between the vaccinia virus DNA and the cowpox DNA. Using known restriction maps for related viruses (Mackett and Archard 1978, Drillien and Spehner 1983), it is possible to establish the origin of most of the fragments of the recombinants and to draw their restriction maps (FIG. 1).

It is seen that the recombinants designated 4, 6, 14, 15 and 19 which are capable of multiplying in CHO cells have retained the characteristic sites of the left end of the cowpox genome. The other recombinants designated 2, 7, 11, 16 and 18 which are incapable of multiplying in CHO cells have only a part or none of these sites of the left end of the cowpox genome.

It follows from these results that the retention of the restriction sites of the left end of the cowpox genome is associated with the phenotype of multiplication on CHO cells.

EXAMPLE 2

Isolation and analysis of the genome of the vaccinia virus recombinants, which has integrated a cowpox DNA fragment In order to define more accurately the localization of useful genetic information, recombinants capable of multiplying on CHO cells were selected after infection with the vaccinia virus and transfection with cowpox DNA fragments.

Figure 2:
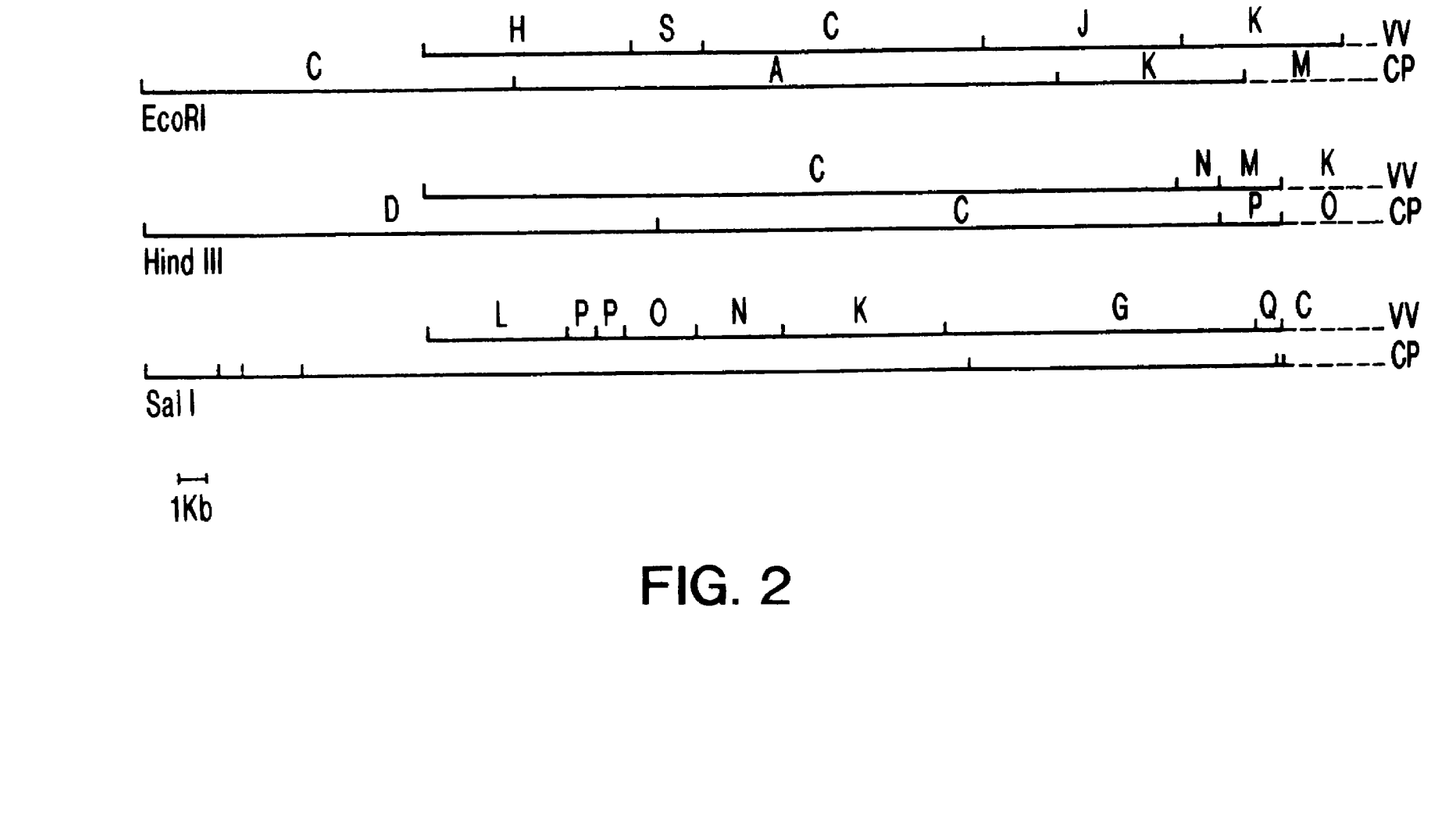
FIG. 2 Restriction maps for the Left end of the vaccinia virus (VV) and cowpox (CP) after cutting with the enzymes EcoRI, HindIII and SaLII.

The restriction fragments useful for the analysis of the portion which is important, i.e. the left end of the two viruses, are shown in FIG. 2; the events of recombination described in Example 1 may be expected to occur in this portion of the genome.

Primary cells of thick embryo are infected with the vaccinia virus mutant tsN7 (Drillien et al., 1982) at a rate of 0.1 pfu per cell and transfected with a mixture of intact DNA of the wild strain of the vaccinia virus (Copenhagen strain) and the cowpox DNA (Brighton strain) which has previously been digested with the enzyme HindIII. Controls for transfection without DNA or with the DNA of the vaccinia virus alone are prepared. After incubating for 48 hours at 39.5° C., the cells are frozen, thawed and the virus thus released is titrated on a monolayer of CHO cells which are then covered with the medium containing 1% agar.

Samples originating from cells transfected with the cowpox DNA give many lytic plaques on CHO cells whereas the control samples give none of them.

The plaques visible on CHO cells are taken again individually and the virus they contain is amplified on chick embryo cells. Their DNA is then extracted and analyzed by comparison with the DNA of the two related strains of vaccinia and cowpox. After digesting with the enzyme EcoRI, the DNA fragments are separated by electrophoresis on agarose gel and they are then transferred to a nitrocellulose filter and hybridized with the SalI-K fragment of the vaccinia virus, which is radioactively labelled with $^{32}p$.

Figure 3A:
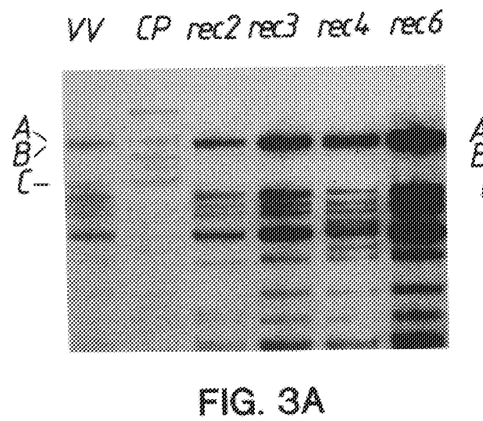
FIG. 3 Characterization of the restriction profiles of the DNA of the recombinants between vaccinia virus and cowpox.
Figure 3B:
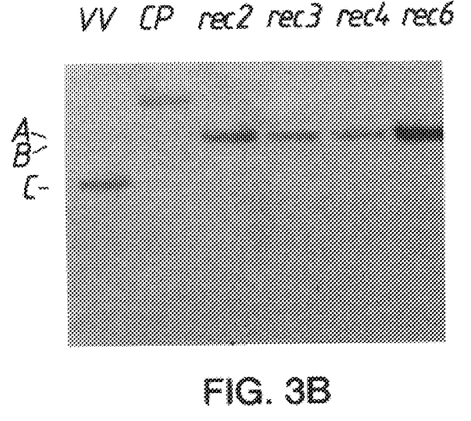

After washing the nitrocellulose in order to remove the non-specifically bound radioactivity, an autoradiograph is prepared. The autoradiograph (FIG. 3) shows that the recombinants of the vaccinia virus which have integrated a cowpox fragment have lost the EcoRI-C fragment which is typical of the vaccinia virus and they contain an EcoRI fragment which hybridizes with the radioactive SalI-K vaccinia fragment; this fragment is intermediate in size between the EcoRI-A fragment of the cowpox and the EcoRI-C fragment of the vaccinia virus.

This new cowpox-vaccinia hybrid EcoRI fragment which is present in all the recombinants, originates from a double recombination between the EcoRI-A fragment of cowpox and the EcoRI-C fragment of vaccinia and must contain the information required for multiplication in CHO cells. For this recombination to take place, it was essential for the information which permits multiplication on CHO cells to be surrounded on either side by sequences of the cowpox genome homologous to the sequences of the vaccinia genome.

EXAMPLE 3

Construction of a recombinant plasmid carrying the region of the cowpox genome, which permits multiplication in CHO cells.

In order to isolate the genetic information which permits multiplication in CHO cells, the EcoRI-A fragment of one of the recombinants described in Example 2 was cloned in the bacterial plasmid pAT153 (Twigg and Sherratt, 1980).

The DNA of one of the recombinants described in Example 2 is purified and then cut with the enzyme EcoRI. The EcoRI-A fragment is eluted from agarose gel and then inserted into the plasmid pAT153 which has previously been subjected to the action of EcoRI. HB101 bacteria are transformed with the ligation mixture and the DNA of the colonies obtained is then transferred onto nitrocellulose and hybridized with the SalI-K fragment of the vaccinia virus. The colonies which are hybridization-positive are amplified and the plasmid DNA they contain is purified. Two plasmids were obtained: pEA1 and pEA2, which correspond to the insertion of the EcoRl-A fragment into the two opposite orientations in the vector pAT153.

In order to verify that these plasmids carry the genetic information which permits the multiplication of the virus on CHO cells, a recombination is induced between the insert of the plasmid DNA and a vaccinia virus: chick embryo cells are infected with the temperature-sensitive mutant tsN7 of the vaccinia virus at a rate of 0.1 pfu per cell and then transfected with the DNA of a wild vaccinia virus and with the DNA of the plasmid PEAL or pEA2. Controls without the DNA of the vaccinia virus or without plasmid are also prepared. After incubating for 48 hours at 39.5° C., the cells are frozen and then thawed and the virus resulting from the infection is titrated on CHO cells. Only the samples originating from the cells transfected with the vaccinia virus DNA and the plasmids pEA1 or pEA2 give plaques on CHO cells.

EXAMPLE 4

Sub-cloning of pEA1 fragments of smaller size in a vector plasmid intended for recombination with the vaccinia virus.

In order to improve the localization of the genetic information which permits the multiplication in CHO cells, restriction fragments which cover smaller portions of the plasmid pEA1 were cloned in a plasmid carrying the thymidine kinase (TK) gene of the vaccinia virus: pTG186poly.

Construction of pTG186poly

The HindIII fragment (Hin-J) of the genome of the vaccinia virus (VV) contains the complete thymidine kinase (TK) gene which has already been used previously to permit the exchange and the recombination of a foreign DNA fragment in the VV genome (Mackett et al., 1982).

It is important to note that the transfer of an insert into the TK gene of the VV genome produces a TK-deficient virus, which facilitates its selection.

It was first of all necessary to produce a plasmid of small size carrying a unique HindIII site which can be used for integrating the Hin-J fragment of VV. AdditionalLy, the unnecessary restriction sites of the plasmid had to be removed so as to enable the subsequent operations to be carried out.

The construction was initiated starting with the plasmid pML2 (Lusky and Botchan, 1981) which is a vector derived from the plasmid pBR322 in which the segment between the nucleotides 1089 and 2491 was lost by spontaneous deletion. The PstI sequence was first removed by inserting the AhaIII-AhaIII fragment of pUC8 (Vioira and Messing, 1982) between the two AhaIII sites of pML3, removing 19 base pairs.

The "linker-tailing" method (Lathe et al., 1984) was employed to insert a HindIII adapter between the NruI and EcoRI sites treated with S1 of this plasmid, removing the BamHI site. This leads to a plasmid with 2049 base pairs carrying the functional β-lactamase gene (which gives ampicillin resistance) and additionally containing an origin of replication which is active in E. coli and a unique HindIII restriction site. This construction was called pTG1H.

The Hin-J fragment of the DNA of VV carrying the TK gene has previously been cloned into the pAT153 vector (Drillien and Spehner, 1983). This 4.6-kb fragment was recloned into the HindIII site of pTG1H. A clone in which the TK gene is located distally relative to the gene coding for ampicillin resistance was selected. This construction was called pTG1H-TK.

The pTG1H-TK construction was used as a vector for the following constructions.

The next step was to isolate a promoter for VV, which can be used to control the expression of the foreign gene to be integrated into VV. The promoter for an early gene coding for a 7,500-dalton (7.5 K) protein has already been successfully used for an identical purpose (Smith et al., 1983), and an isolation of this segment was therefore carried out.

The 7.5 K gene is located on one of the smallest SalI fragments (Sal-S fragment) of the genome of the WR type of VV (Venkatasan et al., 1981). As the small fragments were cloned preferentially, a large proportion of the clones obtained by cloning the DNA of the WR type of VV cut with SalI directly into the pBR322 plasmid carries the Sal-S fragment. This fragment is transferred onto the vector bacteriophage M13mp7O1 (Kieny et al., 1983), by SalI digestion and religation, which gives the phage M13.TG.Sal-S.

In this clone, a ScaI site is present in the immediate proximity of the initiation ATG of the 7.5 K gene. Downstream of the 7.5 K gene there are two unique BamHI and EcoRI sites originating from the vector. The BamHI and ScaI sites are fused using a BglII adapter: 5'-CAGATCTG-3' after filling in the ends generated by BamHI digestion with the Klenow fragment of E. coli polymerase. This method removed the ScaI site, but reconstitutes the BamHI site and moves the unique EcoRI site downstream. At the same time, the SalI (AccI) site downstream is removed, and the SalI site upstream therefore becomes unique. This construction is called M13.TG.7.5K.

Within the Hin-J fragment of the DNA of VV there are ClaI and EcoRI sites which are separated by approximately 30 base pairs (Weir and Moss, 1983). The 7.5 K promoter fragment present in M13.TG.7.5K is excised with AccI and EcoRI and cloned between the ClaI and EcoRI sites of pTG1H-TK in order to produce pTG1H-TK-P7.5K.

In this construction, the unique SamHI and EcoRI sites of the M13 vector are located immediately downstream of the 7.5 K promoter sequence. These unique BamHI and EcoRI sites are used in the following construction.

The polylinker segment of the bacteriophage M13TG131 (Kieny et al., 1983) is excised with EcoRI and BgLII and inserted between the EcoRI and BamHI sites of the plasmid pTG1H-TK-P7.5K, generating pTG186poly. In this construction, 5 unique restriction sites are available for cloning a foreign gene under the control of the P7.5K promoter: PstI, BamHI, SstI, SmaI and EcoRI.

Insertion of the pEA1 fragments into pTG186poly:

The EcORIA fragment of the plasmid pEA1 was digested with different enzymes, and fragments of different sizes were inserted into pTG186poly.

Figure 4:
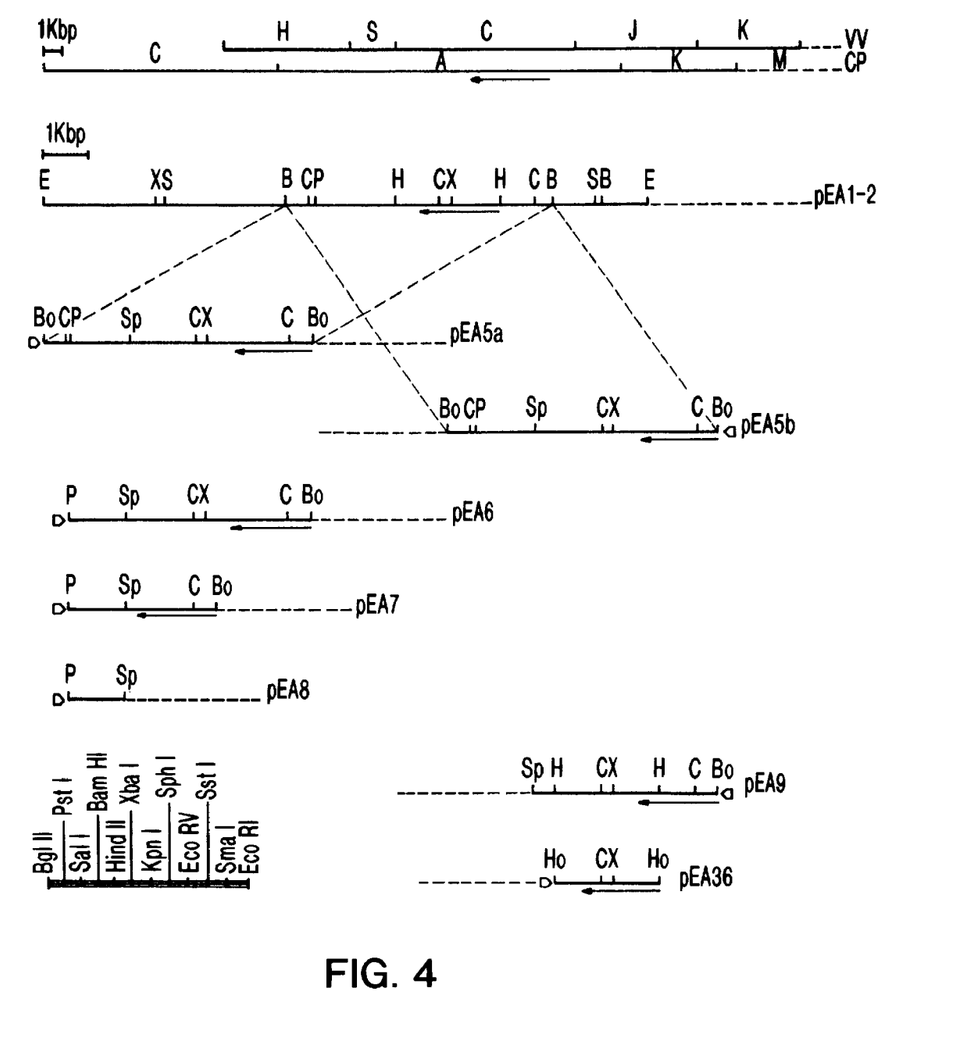

The recombinant plasmids derived from pTG186poly and containing portions of the EcoRI-A fragment of the recombinant plasmid pEA1 are shown in FIG. 4.

Cutting of the plasmid pEA1 with the enzyme BglII gives several fragments. The largest of the BglII fragments was inserted into the BamHI site of the pTG186poly vector to give the plasmids pEA5a and pEA5b which differ by the insertion orientation.

The plasmid pEA6 is derived from the plasmid pEA5a by cutting the latter with the enzyme PstI followed by the recircularization of the largest fragment, which results in the deletion of the BglII-PstI fragment from the plasmid pEA5a.

The plasmid pEA7 originates from pEA6 after cutting the latter with the enzyme ClaI and recircularization of the large fragment obtained, which results in a deletion of the small fragment ClaI.

The plasmid pEA8 originates from pEA6 after cutting the latter with SphI followed by the recircularization of the large fragment, which results in a deletion of the SphI-BgLII fragment on the right.

The plasmid PEA9 originates from the plasmid pEA5b after cutting the latter with SphI followed by religation, which results in a deletion of the SphI-BglIII fragment on the left.

The plasmid PEA36 was constructed in two stages. The small fragment HpaI was first isolated from the plasmid pEA9 and it was inserted into the SmaI site of the M13-130 vector. The HpaI fragment was then taken out of the M13-130 vector using the EcoRI and PstI sites and it was integrated into the EcoRI and PstI sites of the vector pTG186poly.

Each of these plasmids was used in a transfection experiment so as to transfer the insertion present in the TK gene carried by the plasmid to the genome of the vaccinia virus, according to the method described in Example 3.

The plasmids capable of conferring the capacity to multiply in CHO cells to the vaccinia virus are pEA1, 2, 5a, 5b, 6, 9 and 36.

The smallest fragment which has this property is carried by the plasmid pEA36. It contains 2,004 base pairs.

EXAMPLE 5

Sequencing of the gene which permits the multiplication of the vaccinia virus in CHO cells.

Figure 5:
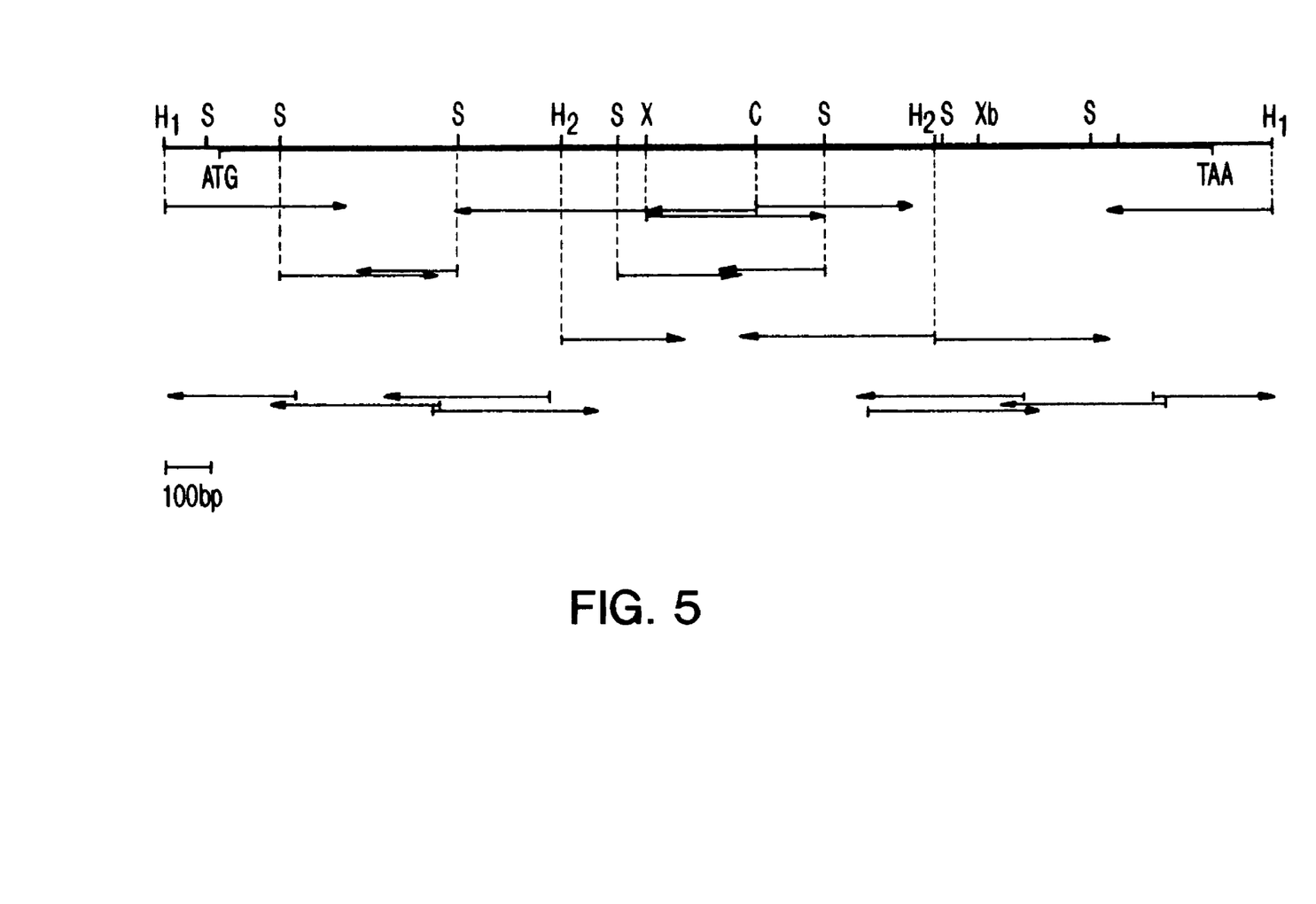

The cowpox DNA carried by the plasmid pEA36 and located between the HpaI sites was completely sequenced by the dideoxynucleotide method (Sanger et al., 1980) after the insertion of the smallest fragments into the phages M13-130 and M13-131 (Kieny et al., 1983) following the strategy outlined in FIG. 5.

The reading frame capable of coding for a 77,000-dalton protein begins at the nucleotides ATG and ends at the nucleotides TAA shown on the map in FIG. 5. The arrows below the map indicate the place where the reading of each clone starts, the length of reading and its direction. When the start of reading does not commence at a restriction site, primers consisting of synthetic oligonucleotides deduced from a partial sequence were employed.

Figure 6A:
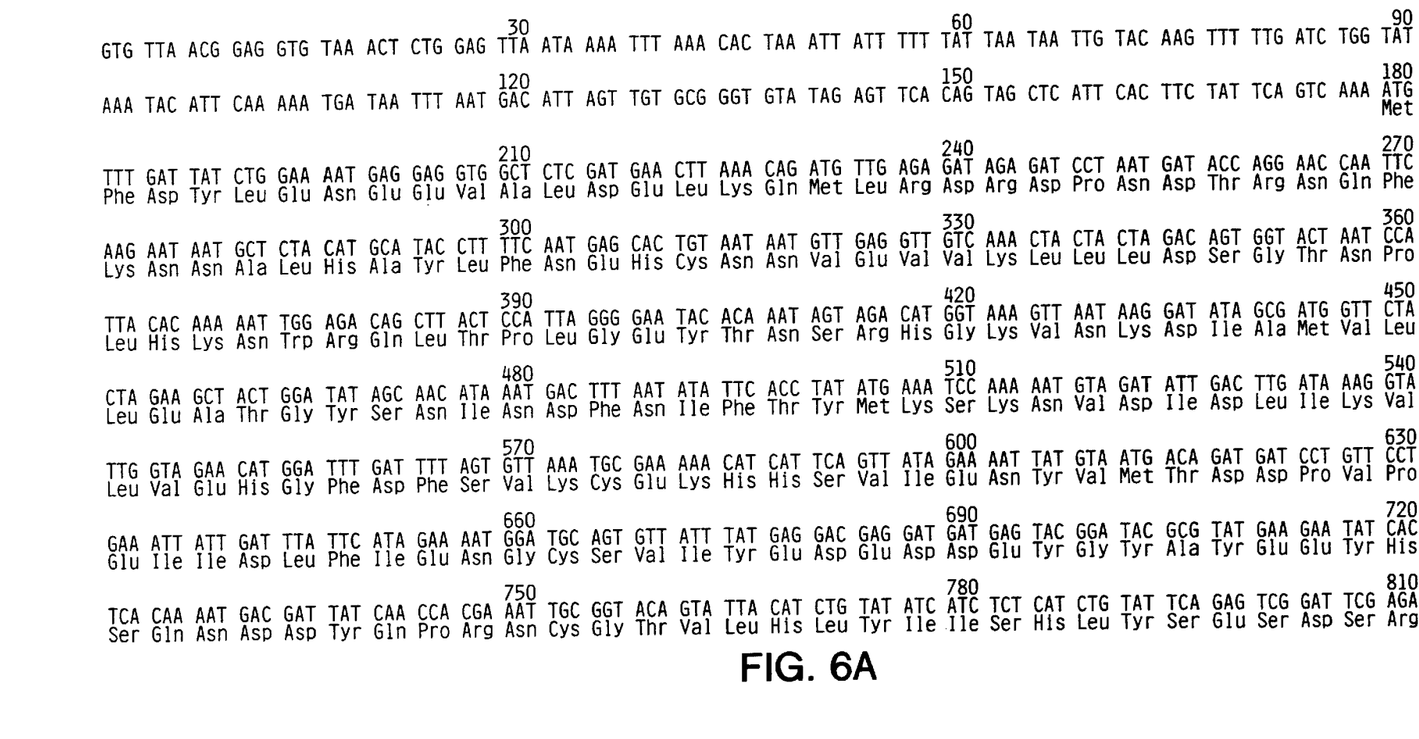
Figure 6B:
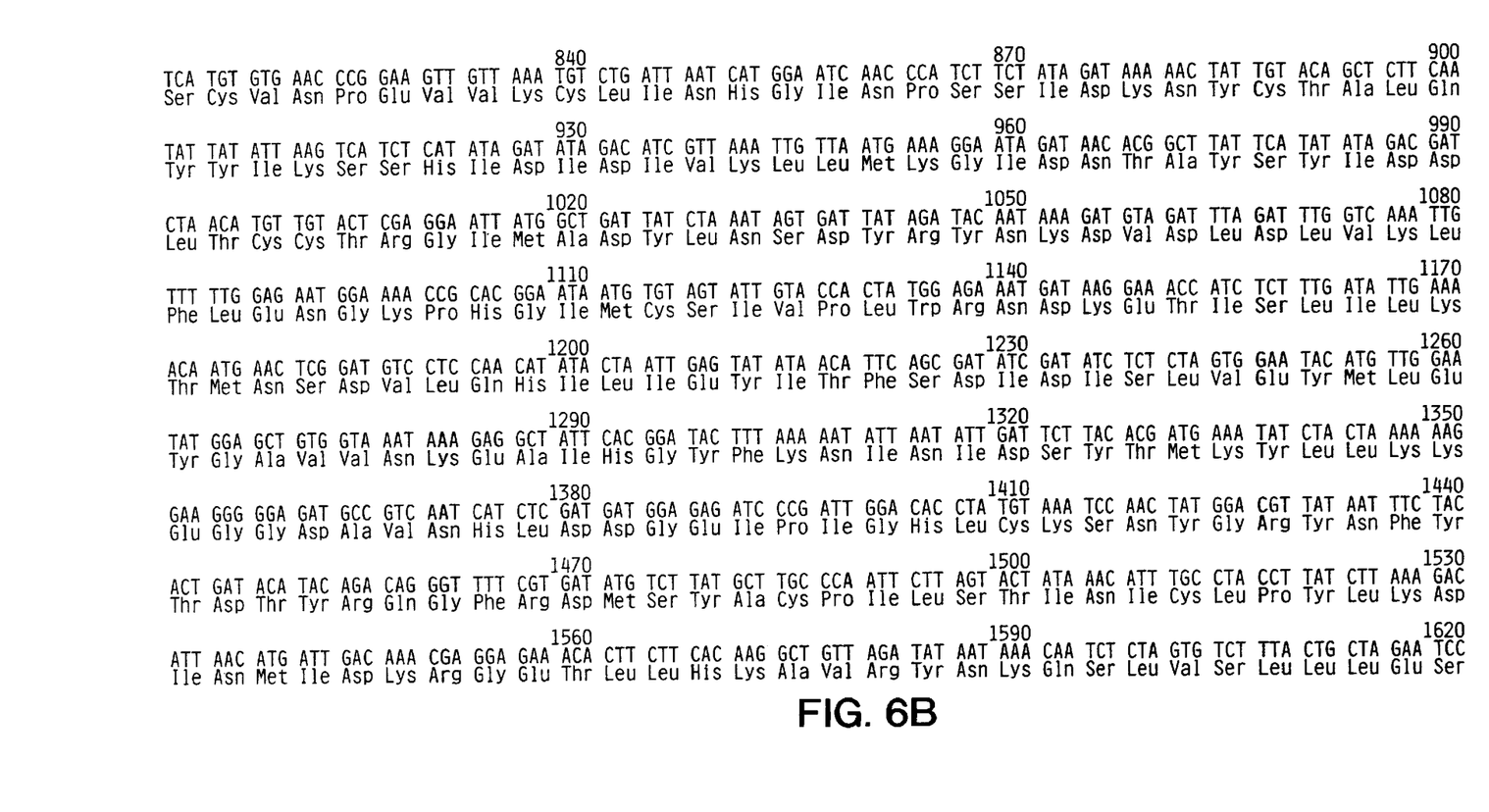

The complete sequence of the gene and the sequence of the 77,000-dalton protein for which it can code are given in FIG. 6.

EXAMPLE 6

Homologous recombination and integration of the cowpox gene into the vaccinia DNA, outside the TK gene.

Among recombinant viruses described in Example 4 and capable of multiplying on CHO cells it is observed that some are TK+ and others TK−.

For example, in the transfection of cells with the plasmid pEA9, out of 27 plaques of recombinant viruses selected for their multiplication on CHO, 16 were TK− and 11 TK+.

The recombination introducing the information which permits the multiplication in CHO cells therefore occurred in a region different from that for the gene which codes for thymidine kinase.

This result implies the possibility of selecting and inserting a foreign gene into a region of the genome other than the TK gene, simultaneously with the selection for multiplication on CHO cells. For this purpose, it is sufficient to juxtapose the gene chosen and the gene which permits growth on CHO cells. The insertion of the latter by homologous recombination with the genome of the vaccinia virus will lead to the co-integration of the foreign gene.

Deposition of representative strain of the invention

The *E. coli* 1106 strain carrying the plasmid pEA36 was deposited at the Collection Nationale de Cultures de Microorganismes (National Collection of Cultures of Microorganisms) under the No. I 594 on Sep. 2, 1986.

The plasmid pEA36 carries a 2.004-bp cowpox virus DNA fragment which permits the multiplication of the virus in CHO cells; this DNA fragment is intended for in vivo recombination with the vaccinia virus (which does not multiply in CHO cells). By transfection of the cells with the DNA plasmid and co-infection with the vaccinia virus, it is possible to select recombinant viruses of vaccinia which have acquired the capacity to multiply on CHO cells.

REFERENCES

Drillien, R., Spehner, D. & Kirn, A. J. Virol. 28, 843–850 (1978).

Drillien, R., Spehner, D. & Kirn, A. Virology 119, 372–381 (1982).

Drillien, R. & Spehner, D. Virology 131, 385–393 (1983).

Kieny, M. P., Lathe, R. & Lecocq, J-P. Gene 26, 91–99 (1983).

Kieny, M. P., Lathe, R., Drillien, R., Spehner. D., Skory, S., Schmitt, D., Wiktor, T., Koprowski, H. & Lecocq, J-P. Nature 312, 163–166 (1984).

Lathe, R., Kieny, M. P., Schmitt, D., Curtis, P. and Lecocq, J-P. J. Molec. Appl. Genet. 2. 331–342 (1984).

Lusky & Botchon Nature 293. 79–81 (1981).

Mackett, M. & Archard, L. C. (1979) J. Gen. Virol. 45, 683–701 (1979).

Mackett, M., Smith, G. L. & Moss, B. P.N.A.S. (USA) 79, 7415–7419 (1982).

Maniatis, T., Fritsch, E. F. & Sambrook, J. "Molecular Cloning: A Laboratory Manual" Cold Spring Harbor Laboratory, Cold Spring Harbor, N.Y. (1982).

Moss, B. In "Virology" (B. N. Fields, ed.) pp. 685–703. Raven Press, New York.

Panicali, D. & Paoletti, E. P.N.A.S. (USA) 79, 4927–4931 (1982).

Panicali, D., Davis, S. W., Weinberg, R. L. & Paoletti, E. P.N.A.S. (USA) 80, 5364–5368 (1983).

Sanger, F. S., Nicklen, S. and Conlson, A. R. P.N.A.S. (USA) 74, 5463–5467 (1977).

Smith G. L., Mackett, M. & Moss, B. Nature 302, 490–495 (1983).

Smith, G. L., Murphy, B. R. & Moss, B. P.N.A.S. (USA) 80, 7155–7159 (1983).

Twigg, A. J. & Sherratt, D. Nature 283, 216–218 (1980).

Venkatasan, S., Baroudy, B. M. & Moss, B. Cell 25, 805–813 (1981).

Viera and Messing Gene 19, 259–268 (1982).

Weir, J. P. & Moss, B. J. Virol. 46, 530–537 (1983).

BRIEF DESCRIPTION OF THE DRAWINGS

The four horizontal lines at the top show the restriction maps for the vaccinia virus (VV) and cowpox (CP), obtained after cutting with the enzymes HindII and XhoI. The next ten horizontal lines show the genomes of the recombinants, isolated according to Example 1, between VV and CP. The restriction sites marked with an arrow are sites characteristic of the cowpox genome; those marked with a vertical line are characteristic of the genome of the vaccinia virus. The sites common to the two genomes are not marked. The broken lines indicate regions of uncertainty in the determination.

The fragments are marked A, B, C etc. in the conventional way in decreasing order of size.

The DNA of vaccinia virus (VV), of cowpox (CP) and of four recombinants called rec2, rec3, rec4 and rec6, isolated according to Example 2, was prepared starting with chick embryo cells infected in the presence of $^3$H-thymidine.

Part A of the figure shows an autoradiograph of the fragments obtained after digestion of DNA with EcoRl, separation of the fragments on agarose gel and autoradiography of the dry gel over a fifteen-day exposure period. In part B, DNA treated in the same way as in A was transferred onto nitrocellulose and hybridized with a SalI-K probe carried by the plasmid pAT153.

FIG. 4 Recombinant plasmids containing portions of the EcoRIA fragment of the plasmid pEA1 integrated into the vector pTG186poly.

The two horizontal Lines at the too show the left end of the DNA of vaccinia virus and cowpox with restriction sites for the enzyme EcoRI. The third line is a linear representation of the plasmid pEA1 with the EcoRI-A fragment as a solid line and the plasmid pAT153 as a broken line.

The lines below are linear representations of the different recombinant plasmids, with the fragment derived from pEA1 as a solid line and the vector pTG186poly as a broken line; the 7.5 K gene promoter is denoted by an outline arrow pointing in the direction of transcription.

The restriction sites are denoted by the following letters:

B BglII

C ClaI

E EcoRI

H HpaI

P Pst1

S SalI

Sp Sph1

X Xho1

FIG. 5 Strategy for sequencing the gene which permits multiplication in CHO cells.

The thick horizontal line shows the DNA fragment sequenced and included between the HpaI sites (H1). The other restriction sites are denoted by the following letters S (Sau3A), H2 (Hpa2), X (XhoI), C (ClaI) and Xb (XbaI). The reading frame capable of coding for an 80,000-dalton protein starts at the nucleotides ATG and finishes at the nucleotides TAA shown on the map. The arrows below the map indicate the place where the reading for each clone begins, the length of reading and its direction.

FIG. 6 Sequence for the gene which permits multiplication in CHO cells.

We claim:

1. A vaccinia virus the genome of which comprises a heterologous DNA sequence, wherein said DNA sequence participates in the multiplication of the vaccinia virus in CHO cells, and further wherein said DNA sequence encodes a protein with an amino acid sequence consisting of the amino acid sequence of FIG. 6.

2. A vaccinia virus according to claim 1, wherein said DNA sequence consists of the nucleotide sequence of FIG. 6.

3. A vaccinia virus according to claim 1, wherein said DNA sequence is operably linked to control elements providing for its expression in a CHO cell.

4. A vaccinia virus according to claim 3 wherein said DNA sequence is operably linked to the native control elements of said DNA sequence.

5. A vaccinia virus according to claim 1, wherein said DNA sequence is inserted in a nonessential region of the vaccinia virus genome.

6. A vaccinia virus according to claim 5, wherein said DNA sequence is inserted in the TK gene of the vaccinua virus genome.

7. A vaccinia virus according to claim 1, wherein the genome of said vaccinia virus further comprises a second heterologous DNA sequence encoding a protein of interest.

8. A vaccinia virus according to claim 5, wherein said second heterologous DNA sequence encoding a protein of interest is also inserted in the TK gene of the vaccinia virus genome.

9. A process for producing a protein of interest which comprises (a) infecting a CHO cell with a vaccinia virus according to claim 7, (b) culturing the infected CHO cell in appropriate conditions, and (c) recovering said protein from the culture.

10. A CHO cell infected with a recombinant vaccinia virus as claimed in claim 7.

11. A CHO cell the genome of which comprises a DNA sequence isolated from cowpox virus, wherein said DNA sequence participates in the multiplication of this virus in CHO cells, and further wherein said DNA sequence encodes a protein with an amino acid sequence consisting of the amino acid sequence of FIG. 6.

12. A CHO cell according to claim 11, wherein said DNA sequence consists of the nucleotide sequence of FIG. 6.

13. A process for producing a protein of interest, comprising (a) infecting a CHO cell according to claim 11 with a recombinant vaccinia virus comprising a heterologous gene encoding said protein of interest;

(b) culturing the infected CHO cell; and (c) recovering said protein of interest from the culture.

14. An isolated DNA sequence which participates in the multiplication of the cowpox virus in CHO cells, wherein said DNA sequence encodes a protein with an amino acid sequence consisting of the amino acid sequence of FIG. 6.

* * * * *